(12) United States Patent
Dhuppad et al.

(10) Patent No.: US 9,078,923 B2
(45) Date of Patent: Jul. 14, 2015

(54) STABLE FIXED DOSE PHARMACEUTICAL COMPOSITION COMPRISING MOMETASONE AND OLOPATADINE

(71) Applicant: Glenmark Pharmaceuticals Limited, Mumbai (IN)

(72) Inventors: Ulhas Dhuppad, Maharashtra (IN); Ashok Katkurwar, Maharashtra (IN); Yashwant Gupta, Maharashtra (IN); Rajesh Ankam, Maharashtra (IN); Chandrakant Dhatrak, Maharashtra (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 14/483,837

(22) Filed: Sep. 11, 2014

(65) Prior Publication Data

US 2015/0079178 A1    Mar. 19, 2015

Related U.S. Application Data

(63) Continuation-in-part of application No. PCT/IB2014/064251, filed on Sep. 4, 2014.

(30) Foreign Application Priority Data

Sep. 13, 2013 (IN) .......................... 2975/MUM/2013

(51) Int. Cl.
| | |
|---|---|
| *A61P 27/14* | (2006.01) |
| *A61K 31/5513* | (2006.01) |
| *A61K 31/575* | (2006.01) |
| *A61K 31/355* | (2006.01) |
| *A61K 9/00* | (2006.01) |
| *A61K 31/573* | (2006.01) |
| *A61K 47/38* | (2006.01) |
| *A61K 31/58* | (2006.01) |
| *A61K 31/335* | (2006.01) |
| *A61K 47/36* | (2006.01) |
| *A61K 47/18* | (2006.01) |
| *A61K 47/26* | (2006.01) |
| *A61K 47/02* | (2006.01) |

(52) U.S. Cl.
CPC ............... *A61K 47/38* (2013.01); *A61K 9/0043* (2013.01); *A61K 31/335* (2013.01); *A61K 31/58* (2013.01); *A61K 47/02* (2013.01); *A61K 47/186* (2013.01); *A61K 47/26* (2013.01); *A61K 47/36* (2013.01)

(58) Field of Classification Search
CPC . A61K 2300/00; A61K 31/335; A61K 31/14; A61K 31/198; A61K 33/42; A61K 9/0043; A61K 31/355; A61K 31/5513; A61K 31/573; A61K 31/575; A61K 47/32; A61K 9/0048; A61K 31/00; A61K 31/445
See application file for complete search history.

(56) References Cited

U.S. PATENT DOCUMENTS

| | | | |
|---|---|---|---|
| 4,871,865 A | 10/1989 | Lever, Jr. et al. | |
| 4,923,892 A | 5/1990 | Lever, Jr. et al. | |
| 5,837,699 A | 11/1998 | Sequeira et al. | |
| 6,127,353 A | 10/2000 | Yuen et al. | |
| 7,977,376 B2 | 7/2011 | Singh et al. | |
| 8,399,508 B2 | 3/2013 | Singh et al. | |
| 2004/0097474 A1 | 5/2004 | Cagle et al. | |
| 2006/0110328 A1* | 5/2006 | Cagle et al. | 424/45 |
| 2008/0058296 A1* | 3/2008 | Chaudry | 514/169 |
| 2012/0121653 A1* | 5/2012 | Jenkins et al. | 424/400 |

FOREIGN PATENT DOCUMENTS

| | | |
|---|---|---|
| WO | WO-0126658 | 4/2001 |
| WO | WO-2006057769 A2 | 6/2006 |
| WO | WO-2009003199 | 12/2008 |
| WO | WO-2010025236 A1 | 3/2010 |
| WO | WO-2011141929 A2 | 11/2011 |
| WO | WO-2012094283 | 7/2012 |
| WO | WO-2014092346 A1 | 6/2014 |

OTHER PUBLICATIONS

Roland et al; Olopatadine nasal spray for the treatment of seasonal allergic rhinitis in patients aged 6 years and older, Expert Opin Pharmacother. 2010, 11(9), 1559-1567.
Bajaj et al; Benefits of Skin Prick Tests for Allergic Rhinitis, The internet Journal of Otorhinolaryngology, 2006, vol. 6, No. 1.
Nsouli S, et al; Combination of a nasal antihistamine olopatadine and a nasal corticosteroid, mometasone . . . , International Scientific Conference, Dubai, UAE, Dec. 2010.
Austin, et al; Mometasone Furoate is a less specific Glucocorticoid than Fluticasone Propionate, European Respitory Journal, 2002, 20, 1386-1392.
Johnson, M., PhD; Development of Fluticasone Propionate and Comparison with other Inhaled Corticosteroids, J Allergy Clin Immunol, Apr. 1998, 101(4), Part 2, S434-S439.
International Search Report, for International Application PCT/IB2014/064251; dated Nov. 19, 2014, pp. 1-13.

* cited by examiner

*Primary Examiner* — Audrea Buckley
(74) *Attorney, Agent, or Firm* — Blank Rome LLP

(57) ABSTRACT

The present invention relates to a stable fixed dose aqueous pharmaceutical composition (e.g., contained in a container) for nasal administration to a human, comprising mometasone or its salt, olopatadine or its salt. The composition may further include a hydrocolloid. The invention also relates to a process for preparing the pharmaceutical composition, and the use of the pharmaceutical composition in the treatment of rhinitis in a subject.

21 Claims, No Drawings

STABLE FIXED DOSE PHARMACEUTICAL COMPOSITION COMPRISING MOMETASONE AND OLOPATADINE

CROSS-REFERENCE TO RELATED APPLICATIONS

This patent application claims priority to (1) Indian Provisional Patent Application number 2975/MUM/2013 (filed on Sep. 13, 2013), and (2) International Patent Application No. PCT/IB2014/064251 (filed on Sep. 4, 2014), each of which is hereby incorporated by reference.

FIELD OF THE INVENTION

The present patent application relates to a stable fixed dose, aqueous pharmaceutical composition for nasal administration to a human comprising mometasone or its salt and olopatadine or its salt. The application also relates to a process for preparing the pharmaceutical composition and its use in the treatment of rhinitis in a subject.

BACKGROUND OF THE INVENTION

Rhinitis is a medical term for irritation and inflammation of the mucous membrane inside the nose Rhinitis may cause additional symptoms, such as sneezing, nasal itching, coughing, headache, fatigue, malaise, and cognitive impairment.

Olopatadine hydrochloride is chemically described as (Z)-11-[3-(dimethylamino)propylidene]-6,11-dihydrodibenz[b,e]oxepin-2-acetic acid hydrochloride, as disclosed in U.S. Pat. Nos. 4,871,865 and 4,923,892. It is commercially available in the U.S as PATANASE® Nasal Spray, which contains 0.6% w/v olopatadine in a non-sterile aqueous solution. It is indicated for the relief of the symptoms of seasonal allergic rhinitis in adults and children 6 years of age and older.

Mometasone furoate is a glucocorticosteroid used topically to reduce inflammation of the skin or in the airways. Mometasone furoate is commercially available as NASONEX® in the U.S. as a nasal spray indicated for upper respiratory conditions such as nasal sinus inflammation. It is available as 50 mcg in a metered-dose, manual pump spray unit containing an aqueous suspension of mometasone furoate monohydrate equivalent to 0.05% w/w mometasone furoate.

WO 2011/141929 discloses an aqueous nasal spray solution comprising fluticasone and olopatadine.

U.S. Pat. No. 6,127,353 discloses a pharmaceutical composition of mometasone furoate monohydrate.

U.S. Pat. Nos. 7,977,376 and 8,399,508 disclose a topical formulation of olopatadine.

WO 2014/092346 discloses a bitter taste masked pharmaceutical composition comprising a corticosteroid, an antihistamine and stevia.

WO 2006/057769 discloses a method of delivering a nasal spray containing olopatadine.

WO 2010/025236 discloses a combination of a nasal steroid and a nasal antihistamine for the treatment of viral upper respiratory tract infections, upper respiratory infections, and common colds.

There still exists a need for easy to use and effective treatments of rhinitis.

SUMMARY OF THE INVENTION

The present invention relates to a stable fixed dose, aqueous pharmaceutical composition for nasal administration to a human. The composition comprises mometasone or its salt and olopatadine or its salt. The pharmaceutical composition may be contained within a container suitable for nasal administration.

One embodiment is a stable fixed dose, aqueous pharmaceutical composition (e.g., contained in a container) for nasal administration to a human, where the composition comprises about 0.001% w/w to about 0.075 w/w mometasone or its salt and about 0.5 w/w to about 0.8% w/w olopatadine or its salt. The pharmaceutical composition may be in the form of a solution or a suspension, but preferably the composition is in the form of a suspension (more preferably, a single phase suspension), wherein mometasone or its salt is present in particle form and olopatadine or its salt is present in dissolved form. In one aspect, the mometasone or its salt and olopatadine or its salt are present in a weight ratio of about 1:3 to about 1:106, or from about 1:5 to about 1:53, or preferably from about 1:5 to about 1:36.

The composition preferably also includes a hydrocolloid. In one embodiment, the composition is a suspension and includes a hydrocolloid in a sufficient amount to prevent phase separation (i.e., separation of the particles and solution) after 3 or 6 months of storage at 25±2° C. and 60%±5% relative humidity (RH) or at 40±2° C. and 75%±5% RH. In one embodiment, the aqueous pharmaceutical composition is a single phase suspension which remains a single phase suspension even after 3 or 6 months of storage at 25±2° C. and 60%±5% RH or at 40±2° C. and 75%±5% RH.

Another embodiment is a stable fixed dose, aqueous pharmaceutical composition (e.g., contained in a container) for nasal administration to a human, where the composition comprises about 0.001% w/w to about 0.075% w/w mometasone furoate monohydrate and about 0.5 w/w to about 0.8% w/w olopatadine hydrochloride.

Yet another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid.

Yet another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid which includes carboxymethylcellulose sodium and xanthan gum. The hydrocolloid may be present at a concentration of at least about 0.1% w/w of the composition.

One embodiment is a stable fixed dose, aqueous pharmaceutical suspension composition (e.g., contained in a container) for nasal administration to a human, comprising about 0.025 w/w to about 0.05 w/w mometasone furoate, about 0.6% w/w to about 0.7% w/w olopatadine hydrochloride and a hydrocolloid, where the hydrocolloid is xanthan gum. The xanthan gum may be present at a concentration of at least about 0.1% w/w, or preferably between about 0.1% w/w to about 3% w/w of the composition.

Another embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid, where the hydrocolloid comprises sodium carboxymethyl cellulose. The sodium carboxymethyl cellulose may be present at a concentration of at least about 0.1% w/w, or preferably between about 0.1% w/w to about 3% w/w of the composition.

Yet another embodiment is a stable fixed dose aqueous pharmaceutical composition in the form of suspension (e.g., contained in a container) for nasal administration to a human, comprising mometasone or its pharmaceutically acceptable salt, olopatadine or its pharmaceutically acceptable salt, a hydrocolloid at a concentration of at least about 0.1% w/w of the composition and a pharmaceutical acceptable excipient.

Suitable pharmaceutical acceptable excipients include, but are not limited to, chelating agents, preservatives, buffers, surfactants, isotonicity agents, taste masking agents, antioxidants, humectants, pH adjusting agents, and mixtures thereof.

In one embodiment, the pharmaceutical composition has a pH between about 3.3 and about 4.1, or between about 3.5 and about 3.9. The inventors discovered that the olopatadine hydrochloride crystallizes out of the fixed dose combination aqueous suspension at a pH of 5 to 5.5. The olopatadine hydrochloride, however, remains dissolved in the aqueous suspension at a pH of about 3.3 to about 4.1.

The aqueous pharmaceutical composition preferably is substantially free of crystals of olopatadine hydrochloride. In one embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition. In another embodiment, the aqueous pharmaceutical composition is substantially free of crystals of olopatadine hydrochloride after 3 or 6 months of storage at 25±2° C. and 60%±5% RH or at 40±2° C. and 75%±5% RH. In yet another embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition, after 3 or 6 months of storage at 25±2° C. and 60%±5% RH or at 40±2° C. and 75%±5% RH.

The osmolality of the pharmaceutical composition may range between about 200 mOsm/kg to about 400 mOsm/kg, or about 250 mOsm/kg to about 350 mOsm/kg.

The viscosity of the pharmaceutical composition may range from about 10 cps to about 200 cps or preferably from about 20 cps to about 150 cps.

In yet another aspect, the pharmaceutical composition is in the form of suspension and contains mometasone furoate in particles having a mean particle size in the range of from about 1 µm to about 20 µm, or preferably from about 1 µm to about 15 µm. In an aspect, the suspension pharmaceutical composition of the present invention has mean particle size of less than 15 µm when determined by microscopy technique.

In yet another aspect, the pharmaceutical composition, when delivered as a nasal spray has spray characteristics comprising a spray pattern having a longest axis of about 15-75 mm, a shortest axis of about 10-65 mm, and an ellipticity of about 1-2.

Another embodiment is a stable fixed dose pharmaceutical composition in the form of a suspension (e.g., contained in a container) for nasal administration to a human, comprising mometasone furoate monohydrate, olopatadine hydrochloride and a hydrocolloid which comprises xanthan gum at a concentration of about 0.3% w/w of the composition, wherein the composition has a pH between about 3.5 to about 3.9.

Yet another embodiment is a stable fixed dose pharmaceutical composition in the form of suspension (e.g., contained in a container) for nasal administration to a human, comprising mometasone furoate monohydrate, olopatadine hydrochloride and a hydrocolloid which comprises sodium carboxymethyl cellulose at a concentration of about 0.5% w/w of the composition, wherein the composition has a pH between about 3.5 to about 3.9.

In a further embodiment, the stable fixed dose, aqueous pharmaceutical composition is contained in a sprayer, and on delivering a spray of the composition to a human nose results in a spray pattern having a longest axis of 15-75 mm, a shortest axis of 10-65 mm, and an ellipticity of 1-2.

One embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 50 mcg of mometasone furoate and (ii) olopatadine hydrochloride equivalent to about 600 mcg olopatadine.

Another embodiment is a method for treating rhinitis, or for administering mometasone and olopatadine. The method includes spraying a stable fixed dose, aqueous pharmaceutical composition comprising mometasone furoate monohydrate, olopatadine hydrochloride and optionally a hydrocolloid such that each spray of the aqueous pharmaceutical composition provides (i) mometasone furoate monohydrate equivalent to about 50 mcg of mometasone furoate and (ii) olopatadine hydrochloride equivalent to about 600 mcg olopatadine.

Yet another embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 25 mcg of mometasone furoate and (ii) olopatadine hydrochloride equivalent to about 600 mcg olopatadine.

Yet another embodiment is a method for treating rhinitis, or for administering mometasone and olopatadine. The method includes spraying a stable fixed dose, aqueous pharmaceutical composition comprising mometasone furoate monohydrate, olopatadine hydrochloride and optionally a hydrocolloid such that each spray of the aqueous pharmaceutical composition provides (i) mometasone furoate monohydrate equivalent to about 25 mcg of mometasone furoate and (ii) olopatadine hydrochloride equivalent to about 600 mcg olopatadine.

In an embodiment, the present invention relates to a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Yet another embodiment is a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable suspension suitable for nasal administration to a human, comprising (a) an aqueous solvent, (b) particles of mometasone furoate suspended in the solvent, the particles having a mean particle size of from about 1 to about 20 μm, (c) olopatadine hydrochloride dissolved in the solvent, and (d) a hydrocolloid, the suspension having a viscosity in the range of about 20 cps to about 150 cps. In one preferred embodiment, the suspension has a pH of about 3.5-3.9, and osmolality in the range of about 250 mOsm/kg to about 350 mOsm/kg. In one embodiment, the suspension further comprises a chelating agent, a preservative, a buffer, a surfactant, an isotonicity agent, and optionally a pH adjusting agent.

Preferably, the suspensions of the present invention have only one phase (i.e., they are preferably a single phase suspension).

In another embodiment, the present invention relates to a method of treating rhinitis in a human in need thereof comprising administering by the nasal route a stable fixed dose, aqueous pharmaceutical composition of the present invention. In one embodiment, the pharmaceutical composition comprises about 0.025% w/w to about 0.05 w/w mometasone or its salt and about 0.5% w/w to about 0.8% w/w olopatadine or its salt, as disclosed herein.

In a further embodiment, the present invention relates to use of a pharmaceutical composition of the present invention for the treatment of rhinitis in a human in need thereof. For example, one embodiment is the use of about 0.025% w/w to about 0.05 w/w mometasone or its salt and about 0.5 w/w to about 0.8% w/w olopatadine or its salt in the preparation of a stable fixed dose, aqueous pharmaceutical composition (e.g., contained in a container) for the treatment of rhinitis in a human in need thereof.

In a further embodiment, the present invention relates to a stable fixed dose, aqueous pharmaceutical composition (e.g., contained in a container) for nasal administration comprising about 0.025 w/w to about 0.05 w/w mometasone or its salt and about 0.5 w/w to about 0.8% w/w olopatadine or its salt for the treatment of rhinitis in a human in need thereof.

In a further embodiment, the present invention relates to a kit comprising a stable fixed dose, aqueous pharmaceutical composition contained in a container, for nasal administration and a package insert containing instructions about the use of the pharmaceutical composition.

DETAILED DESCRIPTION OF THE INVENTION

Definitions

The terms used herein are defined as follows. If a definition set forth in the present application and a definition set forth in a provisional application from which priority is claimed are in conflict, the definition in the present application shall control the meaning of the terms.

The term "effective amount" when used in connection with an active ingredient denotes an amount of the active ingredient that, when administered to a subject for treating rhinitis, produces an intended therapeutic benefit in a subject. The term "active ingredient" (used interchangeably with "active" or "active substance" or "drug") as used herein includes mometasone or its salt and olopatadine or its salt.

In the context of present invention, the effective amount of mometasone or its salt can range from about 0.01 mg to about 10 mg or preferably from about 0.02 mg to about 5 mg. The effective amount of olopatadine or its salt can range from about 0.05 mg to about 20 mg, or preferably from about 0.1 mg to about 15 mg.

In an aspect of this invention, for daily administration by the nasal route, the effective amount of mometasone or its salt can range from about 10 mcg to about 500 mcg, or preferably from about 20 mcg to about 400 mcg, and that for olopatadine or its salt can ranges from about 50 mcg to about 7000 mcg, or preferably from about 100 mcg to about 5400 mcg.

By "salt" or "pharmaceutically acceptable salt", it is meant those salts and esters which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include hydrochloride, furoate, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include sodium, calcium, potassium and magnesium salts.

The term "treating" or "treatment" as used herein includes the prophylaxis, mitigation, prevention, amelioration, or suppression of a disorder modulated by mometasone or its salt or olopatadine or its salt, or by a combination of the two in a mammal.

By "pharmaceutically acceptable excipients", it is meant any of the components of a pharmaceutical composition other than the active ingredients and which are approved by regulatory authorities or are generally regarded as safe for human or animal use.

As used herein, the term "average particle size" (or synonymously, "mean particle size") refers to the distribution of particles, wherein about 50 volume percent of all the particles measured have a size less than the defined average particle size value and about 50 volume percent of all particles measured have a particle size greater than the defined average particle size value. This can be identified by the term "$D_{50}$" or "$d_{(0.5)}$". The average particle size can be measured using various techniques such as microscopy, laser diffraction, photon correlation spectroscopy (PCS) and Coulter's principle.

In the context of present invention, the "hydrocolloid" refers to a colloid system wherein hydrophilic colloid particles (e.g., hydrophilic polymers) are dispersed in water. The hydrocolloid system can exist in gel state or sol (liquid) state. In suspension compositions, the hydrocolloids function as thickening, stabilizing and suspending agents. Non-limiting examples of hydrocolloid include xanthan gum, gum arabic, guar gum, locust bean gum, alginate, starch, agar-agar, carrageenan, gelatin, Avicel RC591® (mixture of microcrystalline cellulose & sodium carboxymethyl cellulose) and cellulose derivatives (e.g., carboxymethyl cellulose sodium). Preferably, the hydrocolloid includes xanthan gum or carboxymethylcellulose sodium.

As used herein, the term "container" refers to single unit-dose container or multi-dose container. Suitable single unit-dose containers or multi-dose containers include, but are not limited to, glass, aluminum, polypropylene or high density polyethylene, for example, high density polyethylene containers produced using a blow-fill-seal manufacturing technique. In one embodiment, the container is a sprayer which delivers the pharmaceutical composition in the form of a fine mist. A sprayer generally includes a container containing a pharmaceutical composition, a pump sealed (e.g., hermetically engaged) with the container, an actuator removably receiving a top portion of the pump, and a cap removably engaged with the container and the actuator.

The present invention relates to a stable fixed dose, aqueous pharmaceutical composition (e.g., contained in a container) for nasal administration to a human, where the composition comprises about 0.001% w/w to about 0.075% w/w mometasone or its salt and about 0.5% w/w to about 0.8% w/w olopatadine or its salt.

The pharmaceutical composition may be in the form of a solution or a suspension, but preferably the composition is in the form of a suspension (more preferably, a single phase suspension), wherein mometasone or its salt is present in particle form and olopatadine or its salt is present in dissolved form. The mometasone or its salt and olopatadine or its salt may be present at a weight ratio of about 1:3 to about 1:106, or from about 1:5 to about 1:53 or preferably from about 1:5 to about 1:36.

The composition preferably also includes a hydrocolloid. In one embodiment, the composition is a suspension and includes a hydrocolloid in a sufficient amount to prevent phase separation (i.e., separation of the particles and solution) after 3 or 6 months of storage at 25±2° C. and 60%±5% relative humidity (RH) or at 40±2° C. and 75%±5% RH. In one embodiment, the aqueous pharmaceutical composition is a single phase suspension which remains a single phase suspension even after 3 or 6 months of storage at 25±2° C. and 60%±5% RH or at 40±2° C. and 75%±5% RH.

The term 'stable' as used in connection with aqueous suspensions refers to a composition when shaken and then stored for at least 24 hours at ambient condition does not show phase separation on visual inspection. Preferably, such stable composition does not show phase separation for a period of at least 3 days, or at least 5 days, or at least 7 days. In one aspect, the 'stable' composition of the present invention shows, upon shaking (e.g., for 1 minute) and visual inspection, no lump formation and a total impurity content of no more than 1.0% after storage at ambient conditions (at about 25° C. and a relative humidity of about 60%) for a period of at least 6 months.

In the context of the present invention, the drug content and impurities can be determined by various analytical techniques such as HPLC, LC-MS, TLC and the like.

It was observed that when various pharmaceutical compositions for nasal administration comprising mometasone or its salt and olopatadine or its salt were prepared, the compositions generally showed physical separation in the suspension composition. This physical instability further leads to lack of dose uniformity. Surprisingly, it was found that addition of a hydrocolloid at certain concentrations (e.g. at a concentration of at least about 0.1% w/w) in the suspension composition yielded a physically stable composition (with no separation) suitable for nasal administration.

Another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid.

Yet another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid which includes carboxymethylcellulose sodium and xanthan gum. The hydrocolloid may be present at a concentration of at least about 0.1% w/w of the composition.

Yet another embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid which comprises xanthan gum. The xanthan gum may be present at a concentration of at least about 0.1% w/w, or preferably between about 0.3% w/w to about 3% w/w of the composition.

Yet another embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid which comprises sodium carboxymethyl cellulose. The sodium carboxymethyl cellulose may be present at a concentration of at least about 0.1% w/w, or preferably between about 0.1% w/w to about 3% w/w of the composition.

Yet another embodiment is a stable fixed dose aqueous pharmaceutical composition in the form of suspension (e.g., contained in a container) for nasal administration to a human, comprising mometasone or its pharmaceutically acceptable salt, olopatadine or its pharmaceutically acceptable salt, a hydrocolloid (e.g., at a concentration of at least about 0.1% w/w of the composition) and a pharmaceutical acceptable excipient.

It will also be appreciated to the skilled artisan that in order to improve the physical properties, appearances, or smells of the composition of the present invention, one or more further pharmaceutically acceptable excipients may be added as desired. Suitable pharmaceutical acceptable excipients include, but are not limited to, chelating agents, preservatives, buffers, surfactants, isotonicity agents, taste masking agents, antioxidants, humectants, pH adjusting agents, and any combination of any of the foregoing.

Suitable surfactants which can be used for preparing aqueous nasal spray composition may include one or more of anionic, cationic, non-ionic or zwitterionic surfactants.

Examples of suitable surfactants which can be employed in the aqueous nasal spray suspension may be selected from, but not limited to, polyethoxylated sorbitan derivatives such as polysorbates, their ether ethoxylates, produced by reaction of sorbitan esters with ethylene oxide, polyoxyethylene alkyl phenol, polyoxyethylene cetyl ether, polyoxyethylene alkyl-aryl ether, polyoxyethylene monolaurate, polyoxyethylene vegetable oil, polyoxyethylene sorbitan monolaurate, polyoxyethylene esters or mixed fatty and resin acids, polyoxyethylene sorbitol lanolin derivative, polyoxyethylene tridecylether, polyoxyethylene sorbitan esters of mixed fatty and resin acids, polyoxyethylene sorbitan monostearate, polyoxyethylene sorbitan monooleate, polyoxyethylene monostearate, polyoxyethylene stearyl ether, polyoxyethylene oleyl ether, polyoxyethylene tridecyl ether, polyoxyethylene fatty alcohol, polyoxyethylene alkyl amine, polyoxyethylene glycol monopalmitate, polyoxyethylene sorbitan monopalmitate, polyoxyethylene cetyl ether, polyoxyethylene oxypropylene stearate, polyoxyethylene lauryl ether, polyoxyethylene lanolin derivative, sodium oleate, quaternary ammonium derivative, potassium oleate, N-cetyl N-ethyl morpholinium ethosulfate, sodium lauryl sulfate or mixtures thereof. Preferred surfactants are polyethoxylated sorbitan derivatives (such as polysorbate 80). The amount of surfactant may range from about 0.001% to about 1% w/w relative to the total weight of the composition.

In order to improve the ability of the aqueous nasal spray suspension to be tolerated on administration to the nasal mucous membrane, it is advantageous to formulate it as isotonic. The osmolality can be set by variation of the amounts of the substances present in the aqueous nasal spray suspension besides mometasone, olopatadine and any further substances present, and/or by addition of an isotonicity agent, preferably a physiologically tolerated salt, such as, for example, sodium chloride or potassium chloride, or a physiologically tolerated polyol, such as, for example, a sugar alcohol, in particular sorbitol or glycerol, in the concentration necessary for rendering isotonic.

Examples of suitable preservatives which can be employed in the aqueous nasal spray suspension include, but are not limited to, benzyl alcohol, quaternary ammonium halides, phenylcarbinol, thimerosal, and disodium edetate. Quaternary ammonium halide preservatives are preferred. Suitable quaternary ammonium halide preservatives include polyquaternium-1 and benzalkonium halides. Preferred benzalkonium halides include benzalkonium chloride and benzalkonium bromide. The amount of the preservative present in the aqueous nasal spray suspension may range from about 0.005 to about 0.2% w/w relative to the total weight of the composition. Preferably, the preservative is present at a concentration of about 0.02% w/w relative to the total weight of the composition.

Examples of suitable chelating agents which can be employed in the aqueous nasal spray suspension include, but are not limited to, edetate disodium (EDTA), edetate trisodium, edetate tetrasodium, and diethyleneamine pentaacetate, preferably EDTA. The amount of the chelating agent present in the aqueous nasal spray suspension of the present invention may range from about 0.0002 to about 0.5% w/w relative to the total weight of the composition.

Examples of suitable buffers which can be employed in the aqueous nasal spray suspension include, but are not limited to, citric acid, acetic acid, fumaric acid, hydrochloric acid, malic acid, nitric acid, phosphoric acid, propionic acid, sulfuric acid, tartaric acid, phosphate salts (e.g., dibasic sodium phosphate, such as dibasic sodium phosphate heptahydrate), or combinations thereof. The suspension of the present invention may comprise an amount of a buffer sufficient to maintain the pH of the composition to from about 3 to about 6. Preferably, the amount of buffer ranges from about 0.005% to about 1% w/w relative to the total weight of the composition.

Examples of suitable sweetener/taste masking agents which can be employed in the aqueous nasal spray suspension include, but are not limited to, sucralose, thaumatin (e.g., Talin$^{(R)}$), sucrose, saccharin (including salt forms such as sodium and calcium salts), fructose, glucose, dextrose, corn syrup, aspartame, acesulfame-K, xylitol, sorbitol, erythritol, ammonium glycyrrhizinate, neotame, mannitol, eucalyptus oil, camphor, and natural or artificial flavors or flavoring agents (for example menthol, mints, vanilla, orange, etc.), or combinations of two or more of such agents. A particularly preferred taste masking agent is sucralose. The amount of the sweetener/taste masking agent present in the aqueous nasal spray suspension may range from about 0.01% to about 1% w/w relative to the total weight of the composition.

Examples of suitable antioxidants which can be employed in the aqueous nasal spray suspension include, but are not limited to, ascorbic acid, alpha-tocopherol (vitamin-E), butylated hydroxyanisole, butylated hydroxytoluene, glutathione, and any combination of any of the foregoing. The amount of the antioxidants present in the aqueous nasal spray composition may range from about 0.0002% to about 0.5% w/w relative to the total weight of the composition.

Examples of suitable humectants which can be employed in the aqueous nasal spray suspension include, but are not limited to, glycerin, sorbitol, polyethylene glycol, propylene glycol or mixtures thereof, which are mixed with a suitable humectant vehicle such as water. The amount of humectant present in the aqueous nasal spray suspension may range from about 0.0002% to about 0.5% w/w relative to the total weight of the composition.

Suitable pH adjusting agents include, but are not limited to, sodium hydroxide and hydrochloric acid.

In the context of present invention, the pharmaceutical stable fixed dose suspension composition for nasal administration may have a pH of between about 3.3 and about 4.1, or between about 3.5 and about 3.9. The inventors discovered that the olopatadine hydrochloride crystallizes out of the fixed dose combination aqueous suspension at a pH of 5 to 5.5. The olopatadine hydrochloride, however, remains dissolved in the aqueous suspension at a pH of about 3.3 to about 4.1.

The aqueous pharmaceutical composition preferably is substantially free of crystals of olopatadine hydrochloride. In one embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition. In another embodiment, the aqueous pharmaceutical composition is substantially free of crystals of olopatadine hydrochloride after 3 or 6 months of storage at 25±2° C. and 60%±5% RH or at 40±2° C. and 75%±5% RH. In yet another embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition, after 3 or 6 months of storage at 25±2° C. and 60%±5% RH or at 40±2° C. and 75%±5% RH.

The osmolality of the composition may range between about 200 mOsm/kg and about 400 mOsm/kg, or about 250 mOsm/kg and about 350 mOsm/kg. The viscosity of the composition may be about 10 cps to about 200 cps or preferably from about 20 cps to about 150 cps.

In yet another aspect, the pharmaceutical composition in the form of suspension and contains mometasone furoate in particles having mean particle size in the range of from about 1 µm to about 20 µm, or preferably from about 1 µm to about 15 µm. In an aspect, the suspension pharmaceutical composition of the present invention has mean particle size of less than 15 µm when determined by microscopy technique.

In yet another aspect, the pharmaceutical composition, when delivered as a nasal spray has a spray pattern having a longest axis of about 15-75 mm, a shortest axis of about 10-65 mm, and an ellipticity of about 1-2.

In the context of present invention, the viscosity can be determined by various known instruments such as a Dynamic stress rheometer or Brookfield viscometer. In a preferred embodiment, the viscosity is determined by a Brookfield viscometer by measuring torque transmission through a sample using a rotating spindle.

In another embodiment, the present invention relates to a stable fixed dose, aqueous pharmaceutical composition (e.g., contained in a container) for nasal administration to a human, where the composition comprises about 0.001% w/w to about 0.075 w/w mometasone furoate monohydrate and about 0.5 w/w to about 0.8% w/w olopatadine hydrochloride.

Another embodiment is a stable fixed dose pharmaceutical composition in the form of suspension (e.g., contained in a container) for nasal administration to a human, comprising mometasone furoate monohydrate, olopatadine hydrochloride and a hydrocolloid which comprises xanthan gum at a concentration of about 0.3% w/w of the composition, wherein the composition has a pH between about 3.5 and about 3.9.

Yet another embodiment is a stable fixed dose pharmaceutical composition in the form of suspension (e.g., contained in a container) for nasal administration to a human, comprising mometasone furoate monohydrate, olopatadine hydrochloride and a hydrocolloid which comprises sodium carboxymethyl cellulose at a concentration of about 0.5% w/w of the composition, wherein the composition has a pH between about 3.5 and about 3.9.

Yet another embodiment is a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Yet another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Yet another embodiment is a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5 w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable suspension suitable for nasal administration to a human, comprising (a) an aqueous solvent, (b) particles of mometasone furoate suspended in the solvent, the particles having a mean particle size of from about 1 to about 20 µm, (c) olopatadine hydrochloride dissolved in the solvent, and (d) a hydrocolloid, the suspension having a viscosity in the range of about 20 cps to about 150 cps. In one preferred embodiment, the suspension has a pH of about 3.5-3.9, and osmolality in the range of about 250 mOsm/kg to about 350 mOsm/kg. In one embodiment, the suspension further comprises a chelating agent, a preservative, a buffer, a surfactant, an isotonicity agent, and optionally a pH adjusting agent.

Preferably, the suspensions of the present invention have only one phase (i.e., they are preferably a single phase suspension).

In a further embodiment, the present invention relates to kit comprising a stable fixed dose, aqueous pharmaceutical composition of the present invention contained in a container for nasal administration and a package insert containing instructions about the use of said pharmaceutical composition. In one preferred embodiment, the container is part of a sprayer which has an actuator. When the actuator is actuated, the composition is delivered in the form of a spray.

In a further embodiment, the pharmaceutical composition is contained in a sprayer, and has, on deliver a spray of the composition to a human nose, a spray pattern having a longest axis of 15-75 mm, a shortest axis of 10-65 mm, and an ellipticity of 1-2.

In the context of present invention, the pharmaceutical composition when delivered as a nasal spray using a sprayer yields a specific spray pattern and spray droplet size. The spray pattern can be determined by various known techniques such as with an ADSA with NSPUA set up (Innova System) and the spray droplet size distribution can be determined by various known techniques such as with a Malvern Spraytec with NSPUA set up (Innova System).

The following describes a typical procedure for characterizing droplet size distribution of the spray—The sprayer is loaded with a composition as described above and primed by an actuating pump via an actuator until a fine mist appears out of the nozzle of the sprayer. A commercially available laser diffraction instrument is arranged so that the nozzle is about 3 cm or 6 cm below the laser beam of the laser diffraction instrument. The pump is actuated with a conventional mechanical actuator using a constant force. The resulting spray of the composition crosses the laser beam. Data are collected for $D_{10}$, $D_{50}$, $D_{90}$, SPAN, and % Volume <10 µm. The average values for each of these parameters for three sprays are calculated.

One embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 50 mcg of mometasone furoate and (ii) olopatadine hydrochloride equivalent to about 600 mcg olopatadine.

Another embodiment is a method for treating rhinitis, or for administering mometasone and olopatadine. The method includes spraying a stable fixed dose, aqueous pharmaceutical composition comprising mometasone furoate monohydrate, olopatadine hydrochloride and optionally a hydrocolloid such that each spray of the aqueous pharmaceutical composition provides (i) mometasone furoate monohydrate equivalent to about 50 mcg of mometasone furoate and (ii) olopatadine hydrochloride equivalent to about 600 mcg olopatadine.

Yet another embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 25 mcg of mometasone furoate and (ii) olopatadine hydrochloride equivalent to about 600 mcg olopatadine.

Yet another embodiment is a method for treating rhinitis, or for administering mometasone and olopatadine. The method includes spraying a stable fixed dose, aqueous pharmaceutical composition comprising mometasone furoate monohydrate, olopatadine hydrochloride and optionally a hydrocolloid such that each spray of the aqueous pharmaceutical composition provides (i) mometasone furoate monohydrate equivalent to about 25 mcg of mometasone furoate and (ii) olopatadine hydrochloride equivalent to about 600 mcg olopatadine.

The stable aqueous nasal spray suspension of mometasone and olopatadine may comprise one or more additional pharmaceutical active agent/s selected from the therapeutic category of, but not limited to, non-steroidal anti-inflammatory agents, decongestants, and any combination of any of the foregoing.

The aqueous nasal spray suspension can be administered as a drop or any other form suitable for topical administration. The composition may also be administered using a nasal tampon or a nasal sponge.

In a preferred embodiment, the aqueous suspension is provided in the form of nasal spray wherein the suspension is administered in a single unit-dose container or multi-dose container. Suitable single unit-dose containers or multi-dose containers include, but are not limited to, glass, aluminum, polypropylene or high density polyethylene, for example, high density polyethylene containers produced using a blow-fill-seal manufacturing technique.

In certain additional embodiments, the invention provides a multi dosage composition of matter, comprising: (a) a multi-unit dosage of a pharmaceutical composition of the present invention; and (b) a container comprising: (i) a squeezable chamber holding the multi dosage of the composition and having an opening wherein the dosage exits the opening when the squeezable chamber is squeezed; and (ii) a closure mechanism removably attached to the opening of the squeezable chamber. In certain embodiments, the multi dosage container is made of a moldable polymer.

In such embodiments, suitable polymers include, but are not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfon (PSF), polyethersulfon (PES), polyacrylate (PAR), and polyamid (PA). In certain embodiments, polymers include polyethylene, particularly medium-density polyethylene (MDPE) (or branched polyethylene) or high density polyethylene (HDPE) (or linear, polyethylene). In one embodiment, the multi dose container is made of high density polyethylene (HDPE).

Other means for delivering the nasal spray, such as inhalation via a metered dose inhaler (MDI), may also be used. Several types of MDIs are regularly used for administration by inhalation. These types of devices can include breath-actuated MDIs, spacer/holding chambers in combination with MDIs, and nebulizers. The term "MDI" as used herein refers to an inhalation delivery system comprising, for example, a canister containing a mixture of an active agent and a propellant optionally with one or more excipients, a metered dose valve, an actuator, and a mouthpiece. The canister is usually filled with a suspension of an active agent, such as the nasal spray composition, and a propellant, such as one or more hydrofluoroalkanes [e.g. 1,1,1,2-tetrafluoroethane (HFA-134a) and 1,1,1,2,3,3,3-heptafluoropropane (HFA-227)], chlorofluorocarbons, and alcohols such as ethanol, isopropanol, butanol, propanol or mixtures thereof. When the actuator is depressed a metered dose of the suspension is aerosolized for inhalation. Particles comprising the active agent are propelled towards the mouthpiece where they may then be inhaled by a subject.

The present invention also relates to a method of treating rhinitis in a human in need thereof comprising administering by the nasal route a stable fixed dose, aqueous pharmaceutical composition of the present invention. For example, the pharmaceutical composition which may be contained in a container comprises about 0.025 w/w to about 0.05% w/w mometasone or its salt and about 0.5% w/w to about 0.8% w/w olopatadine or its salt.

In a further embodiment, the present invention relates to use of about 0.025% w/w to about 0.05% w/w mometasone or its salt and about 0.5% w/w to about 0.8% w/w olopatadine or its salt in the preparation of a stable fixed dose, aqueous pharmaceutical composition (e.g., contained in a container) for the treatment of rhinitis in a human in need thereof. Any pharmaceutical composition described herein may be used.

In a further embodiment, the present invention relates to a stable fixed dose, aqueous pharmaceutical composition (e.g., contained in a container) for nasal administration comprising about 0.025 w/w to about 0.05 w/w mometasone or its salt and about 0.5% w/w to about 0.8% w/w olopatadine or its salt for the treatment of rhinitis in a human in need thereof.

Rhinitis in the context of present invention includes, but is not limited to, irritation and inflammation of the mucous membrane inside the nose and nasal and non-nasal symptoms associated therewith. It includes allergic rhinitis, persistent rhinitis, perennial rhinitis, seasonal rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, it includes allergic rhinitis, perennial rhinitis, persistent rhinitis, seasonal rhinitis and nasal and non-nasal symptoms associated therewith.

In the context of present invention, the nasal and non-nasal symptoms associated with allergic rhinitis include sneezing, nasal itching, rhinorrhea (runny nose), nasal obstruction, coughing, ocular pruritis, excess lacrimation, headache, fatigue, common cold (also known as nasopharyngitis, rhinopharyngitis, acute coryza, or cold), malaise and cognitive impairment.

It will be understood that various modifications may be made to the embodiments disclosed herein. Therefore the above description should not be construed as limiting, but merely as exemplifications of preferred embodiments. Other arrangements and methods may be implemented by those skilled in the art without departing from the scope and spirit of this invention.

The following examples are provided to enable one skilled in the art to practice the invention and are merely illustrative of the invention. The examples should not be read as limiting the scope of the invention.

EXAMPLES

Examples 1-2

Suspension Compositions Containing Mometasone Furoate, Olopatadine HCl and Carboxymethylcellulose Sodium

| SN | Ingredient | Example 1 (% w/w) | Example 2 (% w/w) |
|---|---|---|---|
| 1 | Mometasone Furoate monohydrate Eq. to Mometasone furoate | 0.050 | 0.025 |
| 2 | Olopatadine Hydrochloride | 0.665 | 0.665 |
| 3 | Avicel RC 591 (Microcrystalline Cellulose and Carboxymethylcellulose Sodium) | 1.200 | 1.200 |
| 4 | Benzalkonium chloride (50% solution) | 0.040 | 0.040 |
| 5 | Carboxymethylcellulose Sodium (Cekol 2000 P) | 0.500 | 0.500 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| Observations | | | |
| Physical observation on standing for 24 hours | | No phase separation observed | No phase separation observed |
| Mean Particle size by microscopy | | Below 15 µm. | Below 15 µm. |

Manufacturing Procedure:
1. Avicel RC-591 was added in water for injection with homogenization and allowed to hydrate.
2. Carboxymethylcellulose Sodium was dispersed in water for injection and added to step-1.
3. Dibasic sodium phosphate heptahydrate, Sodium chloride, Edetate disodium and Olopatadine were dissolved in water. The pH was adjusted to 2.8-3.2 with Hydrochloric acid.
4. Step-3 was added to Step-1 with homogenization.
5. Polysorbate 80 was dissolved in water for injection. Mometasone Furoate monohydrate was added and stirred to form slurry.
6. Step-5 was added to Step-4 with homogenization.
7. Benzalkonium chloride was dissolved in water for injection.
8. Step-7 was added to Step-6 with homogenization.
9. The pH was checked and adjusted to 3.5-3.9 with HCl and the total weight was adjusted with Water for injection. The osmolality of the composition was about 250-350 mOsm/kg.

The composition was subjected to stability studies at different conditions. The results of the same are as follows:
Container details: Sprayer containing HDPE bottle crimped with pump and fitted with an actuator and cap.

| Stability Study Data | | | | | | |
|---|---|---|---|---|---|---|
| | Initial | | 3 months | | 6 months | |
| Test | Ex. 1 | Ex. 2 | Ex. 1 | Ex. 2 | Ex. 1 | Ex. 2 |
| Stability condition (25° C. ± 2° C. & 60% RH ± 5% RH) | | | | | | |
| pH | 3.61 | | 3.69 | 3.73 | 3.78 | 3.81 |
| Osmolality (mOsm)* | 310 | 308 | 299 | 298 | 302 | 311 |
| Viscosity (cps)** | 32.5 | | 42.5 | 42.3 | 40.6 | 40.9 |
| Weight per ml (g/ml) | 1.01 | | 1.021 | 1.024 | 1.029 | 1.019 |
| Assay of mometasone furoate (% w/w) | 101 | 102.4 | 99.1 | 99.3 | 98.2 | 97.2 |
| Assay of olopatadine hydrochloride (% w/w) | 98.2 | 99.9 | 97.3 | 99.1 | 97.8 | 97.9 |
| Related substances for mometasone furoate | | | | | | |
| Impurity DMCF (%) | 0.02 | 0.03 | 0.09 | 0.10 | 0.14 | 0.17 |
| Any other impurity (%) | 0.04 | | 0.04 | | 0.03 | |
| Total impurities (%) | 0.09 | | 0.23 | 0.29 | 0.31 | 0.34 |
| Related substances for olopatadine hydrochloride | | | | | | |
| Olopatadine E-isomer (%) | 0.08 | | 0.07 | 0.09 | 0.09 | |
| Any other impurity (%) | 0.03 | 0.04 | 0.09 | 0.12 | 0.11 | 0.11 |
| Total impurities (%) | 0.15 | 0.16 | 0.20 | 0.25 | 0.37 | 0.38 |
| Spray Pattern (at 6 cm) | | | | | | |
| Major Axis (mm) | 52 | | 60 | 63 | 59 | 61 |
| Minor Axis (mm) | 43 | 47 | 49 | 53 | 49 | 51 |
| Ellipticity | 1.2 | 1.1 | 1.2 | 1.2 | 1.2 | 1.2 |

-continued

Stability Study Data

|  | Initial | | 3 months | | 6 months | |
|---|---|---|---|---|---|---|
| Test | Ex. 1 | Ex. 2 | Ex. 1 | Ex. 2 | Ex. 1 | Ex. 2 |
| Droplet size distribution (at 6 cm) | | | | | | |
| $D_{10}$ (μm) | 18.91 | 19.45 | 19.26 | 19.70 | 19.33 | 18.88 |
| $D_{50}$ (μm) | 36.39 | 37.61 | 35.96 | 37.34 | 39.28 | 37.85 |
| $D_{90}$ (μm) | 72.46 | 76.44 | 70.29 | 75.78 | 85.42 | 72.07 |
| SPAN | 1.47 | 1.51 | 1.42 | 1.5 | 1.67 | 1.46 |
| Stability condition (40° C. ± 2° C. & 75% RH ± 5% RH) | | | | | | |
| pH | 3.61 | | 3.68 | 3.72 | 3.59 | 3.68 |
| Osmolality (mOsm) | 310 | 308 | 298 | 306 | 305 | 299 |
| Viscosity (cps) | 32.5 | | 45.2 | 42.6 | 41.8 | 41.5 |
| Weight per ml (g/ml) | 1.01 | | 1.023 | 1.019 | 1.026 | 1.025 |
| Assay of mometasone furoate (%) | 101 | 102.4 | 99.8 | 100.4 | 98.3 | 98.4 |
| Assay of olopatadine hydrochloride (%) | 98.2 | 99.9 | 99.3 | 102.5 | 98.7 | 99.7 |
| Related substances for mometasone furoate | | | | | | |
| Impurity DMCF (%) | 0.02 | 0.03 | 0.14 | 0.20 | 0.25 | 0.25 |
| Any other impurity (%) | 0.04 | 0.04 | 0.04 | 0.03 | 0.03 | 0.04 |
| Total impurities (%) | 0.09 | | 0.25 | 0.39 | 0.40 | 0.46 |
| Related substances for olopatadine hydrochloride | | | | | | |
| Olopatadine E-isomer (%) | 0.08 | | 0.07 | 0.08 | 0.08 | 0.09 |
| Any other impurity (%) | 0.03 | 0.04 | 0.21 | 0.18 | 0.31 | 0.30 |
| Total impurities (%) | 0.15 | 0.16 | 0.32 | 0.36 | 0.68 | 0.64 |
| Spray Pattern (at 6 cm) | | | | | | |
| Major Axis (mm) | 52 | 52 | 61 | 58 | 58 | 58 |
| Minor Axis (mm) | 43 | 47 | 50 | 49 | 48 | 49 |
| Ellipticity | 1.2 | 1.1 | 1.2 | 1.2 | 1.2 | 1.2 |
| Droplet size distribution (at 6 cm) | | | | | | |
| $D_{10}$ (μm) | 18.91 | 19.45 | 19.49 | 19.27 | 18.05 | 18.09 |
| $D_{50}$ (μm) | 36.39 | 37.61 | 35.29 | 34.68 | 36.19 | 36.12 |
| $D_{90}$ (μm) | 72.46 | 76.44 | 64.66 | 63.49 | 71.89 | 70.06 |
| SPAN | 1.47 | 1.51 | 1.28 | 1.27 | 1.50 | 1.44 |

*Determined by Advanced Instruments Osmometer (Model 3250).
**Determined by Brookfield viscometer.

Examples 3-4

Suspension Compositions Containing Mometasone Furoate, Olopatadine HCl and Xanthan Gum

| SN | Ingredient | Example 3 (% w/w) | Example 4 (% w/w) |
|---|---|---|---|
| 1 | Mometasone Furoate monohydrate Eq. to Mometasone furoate | 0.050 | 0.025 |
| 2 | Olopatadine HCl | 0.665 | 0.665 |
| 3 | Avicel RC 591 (Microcrystalline Cellulose and Carboxymethylcellulose Sodium) | 1.000 | 1.000 |
| 4 | Benzalkonium chloride (50% solution) | 0.040 | 0.040 |
| 5 | Xantural 75 (Xanthan Gum) | 0.300 | 0.300 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| Observations | | | |
| Physical observation on standing for 24 hours | | No phase separation observed | No phase separation observed |
| Mean Particle size by microscopy | | Below 15 μm. | Below 15 μm. |

Manufacturing Procedure:

1. Avicel RC-591 was added in Water for injection with homogenization and allowed to hydrate.
2. Xanthan gum was dispersed in Water for injection and added to step-1.
3. Dibasic sodium phosphate heptahydrate, Sodium chloride, Edetate disodium and Olopatadine were dissolved in water. The pH was adjusted to 2.8-3.2 with Hydrochloric acid.
4. Step-3 was added to Step-1.
5. Polysorbate 80 was dissolved in water for injection. Mometasone Furoate monohydrate was added to it and stirred to form slurry.
6. Step-5 was added to Step-4 with homogenization.
7. Benzalkonium chloride was dissolved in water for injection.
8. Step-7 was added to Step-6 with homogenization.

9. The pH was checked and adjusted to 3.5-3.9 with HCl and the weight was adjusted with water for injection. The osmolality of the composition was about 250-350 mOsm/kg.

The composition was subjected to stability studies at different conditions. The results of the same are as follows:
Container details: Sprayer containing HDPE bottle crimped with pump and fitted with a actuator and cap

| | Stability Study Results | | | | | |
|---|---|---|---|---|---|---|
| | Initial | | 3 months | | 6 months | |
| Test | Ex. 3 | Ex. 4 | Ex. 3 | Ex. 4 | Ex. 3 | Ex. 4 |
| Stability condition (25° C. ± 2° C. & 60% RH ± 5% RH) | | | | | | |
| pH | 3.65 | 3.67 | 3.78 | 3.65 | 3.70 | 3.62 |
| Osmolality (mOsm) | 307 | 312 | 302 | 316 | 308 | 308 |
| Viscosity (cps) | 124.2 | 129.1 | 127.9 | 129.9 | 126.2 | 126.8 |
| Weight per ml (g/ml) | 1.015 | 1.022 | 1.02 | 1.023 | 1.02 | 1.019 |
| Assay of mometasone furoate (%) | 99.9 | 102.8 | 102.2 | 99.0 | 98.7 | 100.4 |
| Assay of olopatadine hydrochloride (%) | 99.2 | 100.7 | 99.7 | 99.7 | 99.4 | 99.6 |
| Related substances for mometasone furoate | | | | | | |
| Impurity DMCF (%) | 0.02 | 0.02 | 0.04 | 0.05 | 0.03 | 0.05 |
| Any other impurity (%) | 0.03 | | 0.04 | | 0.03 | 0.04 |
| Total impurities (%) | 0.11 | 0.10 | 0.15 | 0.16 | 0.12 | 0.16 |
| Related substances for olopatadine hydrochloride | | | | | | |
| Olopatadine E-isomer (%) | 0.08 | 0.07 | 0.09 | 0.11 | 0.11 | 0.10 |
| Any other impurity (%) | 0.03 | 0.04 | 0.05 | 0.05 | 0.08 | 0.08 |
| Total impurities (%) | 0.18 | 0.15 | 0.24 | 0.20 | 0.33 | 0.33 |
| Spray Pattern (at 6 cm) | | | | | | |
| Major Axis (mm) | 46 | | 59 | 59 | 56 | 54 |
| Minor Axis (mm) | 38 | | 47 | 44 | 35 | 43 |
| Ellipticity | 1.2 | | 1.3 | 1.4 | 1.6 | 1.3 |
| Droplet size distribution (at 6 cm) | | | | | | |
| $D_{10}$ (μm) | 21.58 | 21.03 | 20.95 | 20.27 | 18.73 | 18.34 |
| $D_{50}$ (μm) | 40.44 | 39.79 | 37.86 | 37.93 | 36.66 | 36.16 |
| $D_{90}$ (μm) | 78.25 | 77.55 | 74.07 | 74.93 | 70.63 | 70.99 |
| SPAN | 1.40 | 1.42 | 1.40 | 1.44 | 1.41 | 1.45 |
| Stability condition (40° C. ± 2° C. & 75% RH ± 5% RH) | | | | | | |
| pH | 3.65 | 3.67 | 3.70 | 3.77 | 3.78 | 3.65 |
| Osmolality (mOsm) | 307 | 312 | 309 | 305 | 302 | 316 |
| Viscosity (cps) | 124.2 | 129.1 | 129.6 | 124.3 | 127.9 | 129.9 |
| Weight per ml (g/ml) | 1.015 | 1.022 | 1.017 | 1.027 | 1.022 | 1.020 |
| Assay of mometasone furoate (%) | 99.9 | 102.8 | 101.7 | 100.6 | 99.6 | 98.9 |
| Assay of oloptadine hydrochloride (%) | 99.2 | 100.7 | 99.9 | 99.4 | 99.7 | 99.9 |
| Related substances for mometasone furoate | | | | | | |
| Impurity DMCF (%) | 0.02 | 0.02 | 0.10 | 0.12 | 0.10 | 0.12 |
| Any other impurity (%) | 0.03 | 0.03 | 0.02 | 0.03 | 0.05 | 0.03 |
| Total impurities (%) | 0.11 | 0.10 | 0.20 | 0.22 | 0.18 | 0.21 |
| Related substances for olopatadine hydrochloride | | | | | | |
| Olopatadine E-isomer (%) | 0.08 | 0.07 | 0.12 | 0.13 | 0.11 | 0.11 |
| Any other impurity (%) | 0.03 | 0.04 | 0.06 | 0.06 | 0.12 | 0.12 |
| Total impurities (%) | 0.18 | 0.15 | 0.26 | 0.26 | 0.41 | 0.40 |
| Spray Pattern (at 6 cm) | | | | | | |
| Major Axis (mm) | 46 | 46 | 56 | 58 | 54 | 55 |
| Minor Axis (mm) | 38 | 38 | 45 | 49 | 34 | 43 |
| Ellipticity | 1.2 | 1.2 | 1.3 | 1.2 | 1.6 | 1.3 |
| Droplet size distribution (at 6 cm) | | | | | | |
| $D_{10}$ (μm) | 21.58 | 21.03 | 20.67 | 23.16 | 19.13 | 19.16 |
| $D_{50}$ (μm) | 40.44 | 39.79 | 38.06 | 39.08 | 37.34 | 37.26 |
| $D_{90}$ (μm) | 78.25 | 77.55 | 75.63 | 69.37 | 72.36 | 72.49 |
| SPAN | 1.40 | 1.42 | 1.44 | 1.19 | 1.42 | 1.43 |

Comparative Examples A and B

Suspension Composition Containing Mometasone Furoate, and Olopatadine HCl

|  |  | Example (% w/w) | |
|---|---|---|---|
| SN | Ingredient | A | B |
| 1 | Mometasone Furoate monohydrate Eq. to Mometasone furoate | 0.050 | 0.050 |
| 2 | Olopatadine HCl | 0.665 | 0.665 |
| 3 | Avicel RC 591 (Microcrystalline Cellulose and Carboxymethyl cellulose Sodium) | 1.00 | 1.00 |
| 4 | Benzalkonium chloride (50% solution) | 0.040 | 0.040 |
| 5 | Carboxymethylcellulose Sodium (Cekol 2000 P) | 0.00 | 0.150 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
|  | Observations | | |
|  | pH | 3.7 | 3.7 |
|  | Physical observation on standing for 24 hours | Phase separation observed | Phase separation observed |

Manufacturing Procedure:

The manufacturing procedure as mentioned in Example 1 was followed.

Comparative Examples C and D

Suspension Composition Containing Mometasone Furoate and Olopatadine HCl

|  |  | Example (% w/w) | |
|---|---|---|---|
| SN | Ingredient | C | D |
| 1 | Mometasone Furoate monohydrate Eq. to Mometasone furoate | 0.050 | 0.050 |
| 2 | Olopatadine HCl | 0.665 | 0.665 |
| 3 | Avicel RC 591 (Microcrystalline Cellulose and Carboxymethyl cellulose Sodium) | 1.000 | 1.000 |
| 4 | Benzalkonium chloride (50% solution) | 0.040 | 0.040 |
| 5 | Xantural 75 (Xanthan Gum) | 0.00 | 0.20 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
|  | Observations | | |
|  | pH | 3.73 | 3.70 |
|  | Physical observation on standing for 24 hours | Phase separation observed | Phase separation observed |

Manufacturing Procedure:

The manufacturing procedure as mentioned in Example 3 was followed.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described.

All publications, patents, and patent applications cited in this application are herein incorporated by reference to the same extent as if each individual publication, patent, or patent application was specifically and individually indicated to be incorporated herein by reference.

We claim:

1. A stable fixed dose aqueous pharmaceutical composition for nasal administration to a human, the composition being a single phase suspension which comprises (a) about 0.001% w/w to about 0.075% w/w mometasone or its salt in particulate form; (b) about 0.5% w/w to about 0.8% w/w olopatadine or its salt in dissolved form; and (c) a hydrocolloid system in an amount sufficient to inhibit phase separation for at least 24 hours when stored at 25±2° C. and 60% ±5% relative humidity.

2. The pharmaceutical composition of claim 1, wherein the mometasone or its salt and the olopatadine or its salt are present in a weight ratio of about 1:3 to about 1:106.

3. The pharmaceutical composition of claim 1, wherein the mometasone salt is mometasone furoate and the olopatadine salt is olopatadine hydrochloride.

4. The pharmaceutical composition of claim 1, wherein the mometasone or its salt has a mean particle size in the range of about 1 μm to about 20 μm.

5. The pharmaceutical composition of claim 1, wherein the composition has a pH of about 3.3 to about 4.1.

6. The pharmaceutical composition of claim 4, wherein the suspension comprises a sufficient amount of a hydrocolloid system to inhibit phase separation for at least 7 days of storage at 25±2° C. and 60%±5% relative humidity.

7. The pharmaceutical composition of claim 1, wherein the composition has a pH of about 3.3-4.1, and an osmolality in the range of about 200 mOsm/kg to about 400mOsm/kg.

8. The pharmaceutical composition of claim 1, wherein the composition has a viscosity in the range of about 20 cps to about 150 cps.

9. A stable fixed dose pharmaceutical composition for nasal administration to a human, said composition is a single phase aqueous suspension comprising (1) about 0.025% w/w to about 0.05% w/w mometasone or its salt in particulate form, (2) about 0.6% w/w to about 0.7% w/w olopatadine or its salt in dissolved form, and (3) a hydrocolloid system in an amount sufficient to inhibit phase separation for at least 24 hours when stored at 25±2° C. and 60%±5% relative humidity.

10. The pharmaceutical composition of claim 9, wherein the composition comprises about 0.025% w/w mometasone furoate.

11. The pharmaceutical composition of claim 9, wherein the composition comprises about 0.05% w/w mometasone furoate.

12. The pharmaceutical composition of claim 9, wherein the composition comprises about 0.665% w/w olopatadine hydrochloride.

13. The pharmaceutical composition of claim 9, wherein the composition further comprises a pharmaceutically acceptable excipient selected from the group consisting of chelating agents, preservatives, buffers, surfactants, isotonicity agent, and any combination of any of the foregoing.

14. The pharmaceutical composition of claim 9, wherein the composition has a pH of about 3.5-3.9, and an osmolality in the range of about 250 mOsm/kg to about 350mOsm/kg.

15. The pharmaceutical composition of claim 9, wherein the composition has a viscosity in the range of about 20 cps to about 150 cps.

16. The pharmaceutical composition of claim 9, wherein the composition has a viscosity in the range of about 20 cps to about 150 cps and is contained in a container, and when delivered as a nasal spray has a spray pattern having a longest axis of 15-75 mm, a shortest axis of 10-65 mm, and an ellipticity of 1-2.

17. A method of treating rhinitis in a human in need thereof comprising administering by the nasal route to the human the pharmaceutical composition of claim 1.

18. The pharmaceutical composition of claim 9, wherein the composition has a pH of 3.3 to 4.1.

19. A stable fixed dose pharmaceutical composition for nasal administration to a human, the composition being a single phase aqueous suspension comprising:
   0.025% or 0.05% w/w mometasone furoate monohydrate;
   0.665% w/w olopatadine hydrochloride;
   0.5% w/w carboxymethyl cellulose sodium;
   1.2% w/w of a mixture of microcrystalline cellulose and carboxymethyl cellulose sodium;
   0.02% w/w benzalkonium chloride;
   0.41% w/w sodium chloride;
   0.01% w/w di-sodium edetate;
   0.94% w/w sodium phosphate heptahydrate; and
   0.01% w/w polysorbate 80;
   wherein the composition has a pH of about 3.3 to about 4.1.

20. The pharmaceutical composition of claim 19, wherein the composition has an osmolality of 250 mOsm/kg to 350 mOsm/kg, a viscosity of 20 cps to 150 cps, and the mometasone furoate monohydrate has a mean particle size of 1 μm to 20 μm.

21. A method of treating rhinitis in a human in need thereof comprising administering by the nasal route to the human the pharmaceutical composition of claim 19.

\* \* \* \* \*